United States Patent [19]

Mushta

[11] Patent Number: 4,512,741

[45] Date of Patent: Apr. 23, 1985

[54] DENTAL INDICATING PASTE AND METHOD OF USE

[76] Inventor: James T. Mushta, 23014 Atlas Rd., Bothell, Wash. 98011

[21] Appl. No.: 294,637

[22] Filed: Aug. 20, 1981

[51] Int. Cl.³ .............................................. A61C 1/00
[52] U.S. Cl. ...................................................... 433/70
[58] Field of Search ......................................... 433/70

[56] References Cited

U.S. PATENT DOCUMENTS

| | | | |
|---|---|---|---|
| 2,993,276 | 7/1961 | Jankelson | 32/1 |
| 3,421,223 | 1/1969 | Stark | 32/19 |
| 3,707,771 | 1/1973 | Guerra | 433/70 |
| 4,198,243 | 4/1980 | Tanaka | 433/70 |

FOREIGN PATENT DOCUMENTS 2715917  10/1978  Fed. Rep. of Germany ........ 433/70

OTHER PUBLICATIONS

Brochure for a MAX-it Product manufactured by Aero-Dent, Inc.

Mixture of Crisco Shortening and Zinc-Oxide used by Prior Art Dentists.

A-17 Normal Butane used as an Aerosol Propellant.

*Primary Examiner*—Robert Peshock
*Attorney, Agent, or Firm*—Gregory W. Moravan

[57] ABSTRACT

An aerosol dental indicating paste comprising oils, such as glycerides, blended with indicating powder, such as zinc oxide, to form a soft, creamy paste which is mixed with a liquid hydrocarbon which acts as both a solvent and a propellant for the dental indicating paste and permits the paste to be dispensed from an aerosol spray can in the form of a mist or spray of fine particles. The dental indicating paste is used to locate high spots, contact areas and pressure areas on dentures and dental castings. In use, the dental indicating paste is sprayed on the denture or casting to form a thin coating thereon. The coated denture or casting is then placed in its desired location in the patient's mouth, after which it is removed. Disturbances in the dental indicating paste indicate the location, size and elevation of the problem areas.

10 Claims, No Drawings

DENTAL INDICATING PASTE AND METHOD OF USE

BACKGROUND OF THE INVENTION

The present invention relates to the proper fitting of dentures, as well as to the proper fitting of dental castings such as crowns and inlays. More particularly, it relates to a dental indicating paste used to detect high spots on dentures, also known as contact or pressure areas; and to detect high spots on dental castings which may interfere with a proper fit.

SUMMARY OF THE INVENTION

As is known, the proper fitting of dentures is essential to prevent soreness or irritation of the tissues in the patient's mouth; and in the case of dental castings, it is essential to assure that the casting is properly and fully seated to prevent loss of the casting or other undesireable effects. As used herein, the term denture is defined to include both full dentures and any form of partial denture; and the term casting includes both crowns and inlays, as well as any other form of dental casting.

Accordingly, the primary object of the present invention is to provide a dental indicating paste which will quickly, accurately, and economically aid in the detection of contact or pressure areas on dentures, and to aid in the detection of high spots on dental castings so that the denture or casting can be suitably adjusted to insure the proper fit. Proper use of the dental indicating paste will indicate not only the location of the contact or pressure areas and high spots, but will also indicate their size and, to some degree, their height.

A further object is to provide such a dental indicating paste which can be applied in aerosol form to thereby save time, reduce mess and waste, and increase the ease of proper application of the dental indicating paste to the denture or casting.

Another object is to provide a dental indicating paste which is non toxic, has a pleasant taste, and which is easily cleaned from the patient's mouth and from the denture or casting.

A further object is to provide a method of use of the dental indicating paste.

It is to be understood that the foregoing is but a brief summary of some of the objects, features, advantages and characteristics of the present invention, since these and other objects, features, advantages and characteristics will be apparent from the following more detailed description of the preferred embodiments thereof.

DESCRIPTION OF THE PREFERRED EMBODIMENTS

In broadest form, the dental indicating paste comprises non-toxic oils (defined herein to include solid or liquid animal, vegetable and mineral oils and fats) blended with enough non-toxic indicating powder to form a soft, creamy paste at room temperature. The terms oils and glycerides are further defined to include either the singular or plural sense.

By way of non-limiting example, the dental indicating paste may consist of about 1 part non toxic glycerides to about 2.2 parts non toxic indicating powder, which are warmed and thoroughly blended together to form a relatively soft, creamy paste, having a mushy consistency like that of soft margarine.

If desired, natural or artificial flavorings can be added to give the dental indicating paste a pleasant taste and aroma. The resultant dental indicating paste taste must, of course, comply with all applicable Pure Food and Drug Laws.

The glycerides may be provided, for example, in the form of any suitable liquid or solid vegetable oil, such as liquid soybean oil, cottonseed oil, saffron oil, corn oil, etc. Wesson brand oil manufactured by Hunt-Wesson Foods, Inc. of Fullerton, Calif. 92634, which is a liquid consisting of a mixture of partially hydrogenated soybean oil, cottonseed oil, and polyglycerides, has been found to be satisfactory.

The oils, whether glycerides or not, have several functions. When blended with the indicating powder in the proportions indicated, they form a dental indicating paste having the desired, soft, creamy consistency which is not runny, and which can be dispensed from an aerosol can in the form of a mist or spray. The oils also help the dental indicating paste to adhere to a dry denture or casting, but are relatively non adhering to moist oral tissues, thereby enabling the dental indicating paste to be used in the manner which will be discussed subsequently.

The indicating powder is preferably any suitable substance which is relatively opaque and of a color which contrasts well with that of the denture or casting, such as zinc oxide U.S. P.; although titanium dioxide or magnesium oxide could be used. These compounds, which are oxides of metals, are naturally colored a bright white, but if other colors were desired other compounds possessing the desired coloring could be used; or non toxic coloring could be added as desired.

Although the ratio of 1 part glycerides to 2.2 parts indicating powder is preferred, acceptable results are obtained in the range of about 1 part glycerides to about 1.5 to 2.5 parts indicating powder.

Naturally, it will be apparent to one skilled in the art, in view of the disclosures herein, that the exact proportions of the specific oil used to the specific indicating powder used may vary somewhat from the proportions given above by way of example, without departing from the scope and spirit of the present invention.

After the paste is formed, a measured quantity of it is dispensed into any conventional aerosol spray can along with a suitable quantity of a non toxic propellant of the type which is normally a liquid while in the aerosol can, but is normally a gas at room temperature and pressure. A relatively low pressure, low volatility, orally compatible hydrocarbon propellant is preferred. By way of non limiting example, A-17 (a liquid at 70° F. and 17 p.s.i.) normal butane may be used as the propellant. Higher pressure, more volatile propellants can be used, but they tend to cause excessive dispersion of the dental indicating paste in the air.

The A-17 normal butane also has the feature of having a relatively low vapor pressure, such that a concentration of newly dispensed dental indicating paste may foam or bubble slightly as the butane evaporates, leaving the dispensed dental indicating paste with a textured surface. Such a textured surface may aid in detecting contact or pressure areas on dentures, for example, where the pressures are relatively light and are detected best by a change in the surface texture of the dental indicating paste. The manner of use of the dental indicating paste will be described in more detail subsequently.

It is important that the propellant be a liquid in the aerosol can, since it must also be able to act as a solvent or dilutant for the dental indicating paste. That is, the oils in the dental indicating parts, such as glycerides, must be soluble or disperseable in the propellant. This is because the dental indicating paste is not dispensed from the aerosol can in a solid stream like toothpaste, but is instead dispensed in the form of a fine mist or spray which when applied to the denture or casting makes a coating thereon of the dental indicating paste of the desired, soft, creamy consistency. Thus, in a sense, the dental indicating paste undergoes a sort of phase transformation-being in a soft, creamy paste phase before being added to the aerosol can, being in a liquid phase while mixed in the aerosol can with the propellant, and again forming a soft, creamy paste phase as a coating on the denture or casting to be examined after it is dispensed thereon as a fine mist from the aerosol can.

As used above, the term liquid phase is used broadly, since when the indicating powder comprises an oxide of a metal, for example, the indicating powder is usually fairly insoluble in the propellant, but the indicating paste has still been broken down or liquified, by its oils being dispersed in the propellant, which acts as a solvent.

By way of non limiting example, in a cylindrical aerosol can having a reservoir about 1¼ inches in diameter and about 3½ inches tall, there is placed about 9 grams of dental indicating paste (composed of about 2.2 parts zinc oxide to 1 part Wesson brand oil, for example) mixed with about 17 grams of A-17 normal butane propellant. Thus, about 1 part dental indicating paste to about 1.9 parts propellant will give satisfactory results.

The amount of propellant placed in the aerosol can may be varied somewhat, as long as enough is used to insure that the dental indicating paste is diluted or the oil present therein is dissolved sufficiently such that the dental indicating paste is dispensable from the aerosol can as a fine mist or spray. Use of excessive propellant is wasteful, but it is not harmful to the invention since it merely results in a longer spraying time before a given desired thickness of dental indicating paste can be built up on the denture or casting.

It is preferred that the aerosol can be equipped with any type of conventional metering valve which releases, each time it is depressed, one very short burst or mist or spray of the dental indicating paste, in order to avoid over application of the dental indicating paste on the denture or casting. However, it is possible to use any type of conventional non metering valve which will dispense the dental indicating paste for so long as it is depressed. The valve is also chosen so that it will produce a fine mist or spray, and may have, for example, an orifice about 0.33 millimeters in diameter.

As has been mentioned, the dental indicating paste is used to detect contact or pressure points (high areas) of the mouth tissue engaging portions, or base, or a denture, which may cause soreness or irritation of the mouth tissues. In use, the denture is first washed and dried. Then, a thin layer of dental indicating paste is dispensed onto either the entire surface of the base of the denture, or ot the area which is suspected of being a contact or pressure area. The denture is then seated in the patient's mouth with finger pressure, after which it is removed and examined. The dental indicating paste will be disturbed in those areas on the base of the denture which are problem contact or pressure areas (i.e. too high). The greater the displacement of the dental indicating paste, the heavier the contact or pressure area, i.e. the higher the problem area is. Very light contact or pressure areas may cause only a slight change in the surface texture of the paste. Such a change would indicate, of course, that that portion of the denture was only slightly too high.

By "reading" the areas in which the dental indicating paste has been disturbed, the size, location, and height of the contact or pressure areas can be easily and accurately determined, and the denture may then be suitably adjusted by any conventional technique. The process is repeated as many times as is necessary until all contact or pressure areas of the denture have been eliminated and the denture fits properly.

A similar procedure is followed in using the dental indicating paste to detect high spots of dental castings such as crowns or inlays, except that the dental indicating paste is sprayed on the casting's tooth contacting surfaces, after which the casting is then attempted to be seated on or in the tooth. The dental indicating paste on any portions of the casting which are too high and which thus prevent proper seating of the casting will be disturbed, thereby indicating the location and size of the troublesome high spots. This, of course, enables suitable adjustments to the casting and/or tooth to be made, which can be performed by any conventional technique. The process is repeated until the casting seats properly on or in its tooth.

After the denture or casting fits properly, the dental indicating paste can be easily removed therefrom with soap and warm water.

From the foregoing, various further applications, modifications, and adaptations of the present invention will be apparent to those skilled in the art to which the present invention is addressed, within the scope of the claims which are appended hereto.

I claim:

1. An aerosol dental indicating paste for detecting high spots on dental articles, wherein the paste comprises oils blended with indicating powder to form an easily displaceable paste which is non toxic, and is soft and creamy at room temperature, wherein said paste is packaged in an aerosol spray can means mixed with a propellant which is normally a liquid while within the spray can and which is normally a gas at room temperature and pressure, wherein the type and quantity of said propellant is chosen such that said paste is dispensable from said aerosol can in the form of a mist of very fine particles which form a layer of said soft, creamy paste on said dental article when dispensed thereon to enable high spots on said dental article to be detected by displacement of said soft, creamy paste; and wherein said oils in said paste are soluble in said propellant in said aerosol can to enable said paste to be liquified to be dispensed in the form of a mist of fine particles, and wherein said paste is in a soft and creamy, easily displaceable paste phase once again after being dispensed onto said dental article.

2. The dental indicating paste according to claim 1 wherein said propellant is selected to be relatively non-volatile to ensure that when said paste is dispensed onto said dental article some of said liquid propellant will be conveyed to said dental article along with said paste to ensure that as said liquid propellant changes to said gas at room temperature on said dental article it will cause said paste to bubble, giving said paste a textured surface which is useful in detecting high, contact and pressure areas of said dental article when it is being fitted in the mouth of a patient.

3. The dental indicating paste according to claims 1 or 2, wherein said oils comprise glycerides comprising vegetable oil.

4. The dental indicating paste according to claims 1 or 2, wherein said oils comprise glycerides comprisng vegetable oil.

5. The dental indicating paste according to claims 1 or 2, wherein said oils comprise glycerides, and wherein there are about 1 part glycerides to about 1.5 to 2.5 parts indicating powder.

6. The dental indicating paste according to claim 5, wherein said oils comprise glycerides comprising vegetable oil.

7. The dental indicating paste according to claim 1, wherein said oxide of a metal comprises zinc oxide.

8. The dental indicating paste according to claim 1, wherein the propallant comprises A-17 normal butane.

9. A method comprising the steps of preparing a soft, creamy, easily displaced paste by blending oils with indicating powder, mixing the soft, creamy, easily displaced paste with a propellant in an aerosol can, selecting the propellant to be orally compatible and to be one in which the oils are soluble wherein said propellant at least substantially dissolves the oils in the paste to help liquify the paste in the aerosol can so the paste can be sprayed from the can in a mist of fine particles, forming a coating of said soft, creamy, easily displaced dental indicating paste on said article by spraying said paste from said aerosol can in the form of fine particles onto said article, seating said article in its intended location in a patient's mouth, removing said article from the patient's mouth, and examining the article for displacements of the soft, creamy, easily displaced dental indicating paste on said article and for changes in the surface texture of said soft, creamy, easily displaced dental indicating paste which indicate high, contact and pressure areas thereon.

10. The method according to claim 9, further comprising the step of selecting the propellant to be relatively non-volatile to ensure that when said paste is dispensed onto said dental article some of said liquid propellant will be conveyed to said dental article along with said paste to ensure that as said liquid propellant changes to said gas at room temperature on said dental article it will cause said paste to bubble, giving said paste a textured surface which is useful in detecting high, contact and pressure areas of said dental article when it is being fitted in the mouth of a patient.

* * * * *